United States Patent [19]

Creech

[11] Patent Number: Plant 6,172

[45] Date of Patent: May 10, 1988

[54] APPLE TREE

[75] Inventor: John V. Creech, Cumberland, Ky.

[73] Assignee: Columbia and Okanogan Nursery, Inc., Wenatchee, Wash.

[21] Appl. No.: 738,268

[22] Filed: May 28, 1985

[51] Int. Cl.[4] ..... A01H 5/03

[52] U.S. Cl. ..... Plt./43

[58] Field of Search ..... Plt./34

*Primary Examiner*—Robert E. Bagwill

*Attorney, Agent, or Firm*—Klarquist, Sparkman, Campbell, Leigh & Whinston

[57] ABSTRACT

An apple tree which is a mutation of the Gala apple variety GALA (KIDD's D-8), wherein the fruit of the new variety presents a bright scarlet red color which extends uniformly over substantially the entire body of the fruit.

1 Drawing Sheet

ORIGIN OF THE VARIETY

This new variety is a mutation of the Gala variety (U.S. Plant Pat. No. 3,637, issued on Oct. 15, 1974) and was found in 1980 by me as a branch sport or mutation on one of several Gala (Kidd's D-8) variety trees growing in my nursery orchard in Cumberland, Ky. I recognized the fruit carried by the branch as being of an attractive and distinctive color, being of a bright scarlet red color which extends uniformly over substantially the entire body of the fruit. I grafted the mutation branch onto an apple rootstock. Asexual reproduction through two generations on several trees shows that the unique scarlet red color comes true to form and is established and transmitted through succeeding asexual propagations. The new variety is named Scarlet Gala variety.

BRIEF DESCRIPTION OF THE DRAWING

The accompanying drawing is an illustration, by photographic reproduction in color, showing fruit of the new variety compared with fruit of other Gala varieties, and in which.

DESCRIPTION OF THE NEW VARIETY

Figure 1:
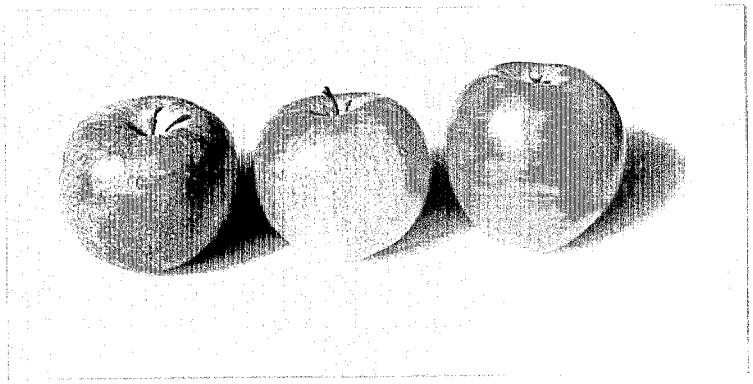
FIG. 1 shows side views taken partly from above of (1) an apple of my new variety (shown at the right in the figure), (2) an apple of the Royal Gala variety (U.S. Plant Pat. No. 4,121, issued on Oct. 4, 1977) (shown at the left of the figure), and (3) an apple of the above noted Gala (Kidd's D-8) variety (shown in the middle in the figure).
Figure 2:
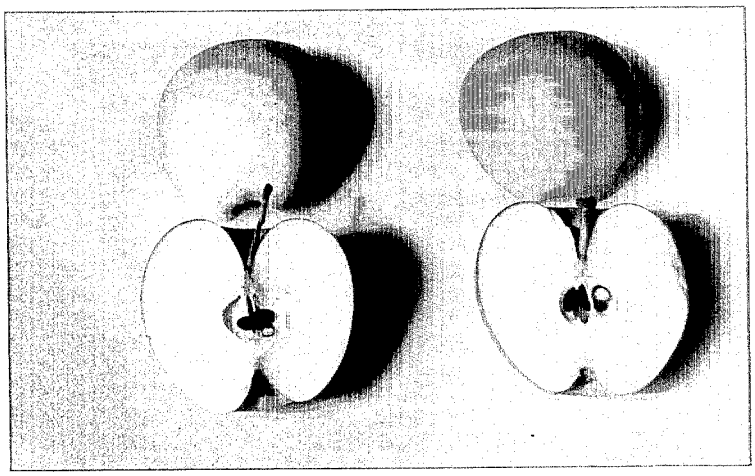
FIG. 2 shows, at the right in the figure, two halves of an apple of my new variety, and at the left in the figure, two halves of an apple of the Gala (Kidd's D-8) variety.
Figure 3:
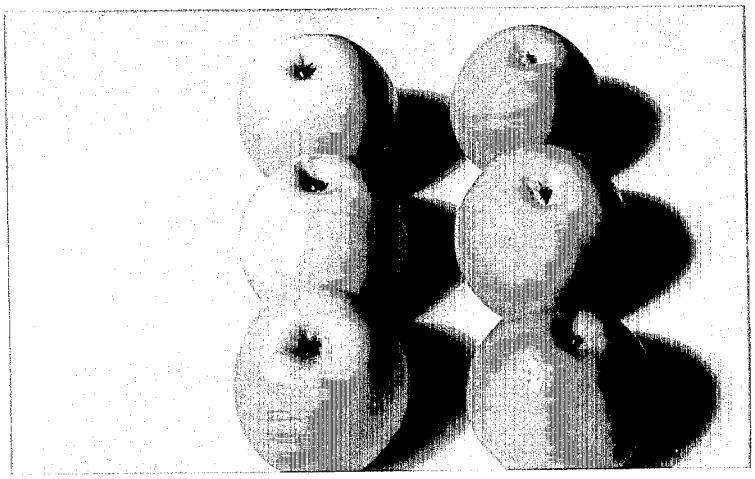
FIG. 3 shows, at the right in the figure, three apples of my new variety and, at the left in the figure, three apples of the Gala (Kidd's D-8) variety, the view showing the bottoms and sides of the apples depicted therein.

The following is a detailed description of my new Scarlet Gala variety with color terminology in accordance with Ridgway's Color Standards and Nomenclature, 1912 edition, except where general color terms of ordinary dictionary significance are obvious.

Locality where grown and observed: Cumberland, Ky., U.S.A.

Tree:

*Trunk, branches, leaves and flowers.*—Similar to those of Gala (Kidd's D-8) variety, as disclosed in U.S. Plant Pat. No. 3,637, made of reference herein.

Fruit:

*Size, form, cavity and basin.*—Similar to those of Gala (Kidd's D-8) variety, as disclosed in U.S. Plant Pat. No. 3,637.

Stem: Shorter and thicker than that of Gala (Kidd's D-8) variety, as disclosed in U.S. Plant Pat. No. 3,637 and of Royal Gala, as disclosed in U.S. Plant Pat. No. 4,121 made of reference herein.

Calyx: Similar to that of Gala (Kidd's D-8) variety, as disclosed in U.S. Plant Pat. No. 3,637, and of Royal Gala, as disclosed in U.S. Plant Pat. No. 4,121 except that calyx is smaller and calyx basin is smaller and shallower.

Skin: Thin, tough, smooth, glossy, waxed.

Ground color: Plate I, color row i, column 3 O-R "Nopal Red" of Ridgway Color Standard and Nomenclature, very bright and uniformly distributed over substantially the whole area of the fruit. Color of

*Dots.*—Yellow, but inconspicuous.

*General color effect.*—Glossy and bright scarlet red over substantially the whole area of the fruit.

Flesh:

*Core and seeds.*—Similar to those of Gala (Kidd's D-8) variety, as disclosed in U.S. Plant Pat. No. 3,637.

Use: Market; dessert.

Keeping quality: Good.

Resistance to:

*Insects.*—Good.

*Diseases.*—Good.

I claim:

1. A new and distinctive variety of apple tree which is a mutation of the Gala variety (U.S. Plant Pat. No. 3,637) substantially as shown and described, characterized—in comparison with said Gala variety and with the Royal Gala variety (U.S. Plant Pat. No. 4,121—by a brighter and scarlet red color uniformly distributed over substantially the whole area of the fruit, by a smaller calyx and calyx basin, and by a shorter and thicker stem.

* * * * *